US011352255B2

(12) United States Patent
McKay et al.

(10) Patent No.: US 11,352,255 B2
(45) Date of Patent: Jun. 7, 2022

(54) PROCESS FOR PURIFYING A CONTAMINATED HYDROCHLORIC ACID COMPOSITION

(71) Applicant: Avantium Knowledge Centre B.V., Amsterdam (NL)

(72) Inventors: Benjamin McKay, Amsterdam (NL); Johannes Hendrick Vleeming, Breda (NL); Wei Zhao, Breda (NL)

(73) Assignee: Avantium Knowledge Centre B.V., Amsterdam (NL)

( * ) Notice: Subject to any disclaimer, the term of this patent is extended or adjusted under 35 U.S.C. 154(b) by 536 days.

(21) Appl. No.: 16/466,990

(22) PCT Filed: Dec. 11, 2017

(86) PCT No.: PCT/EP2017/082219
§ 371 (c)(1),
(2) Date: Jun. 5, 2019

(87) PCT Pub. No.: WO2018/108811
PCT Pub. Date: Jun. 21, 2018

(65) Prior Publication Data
US 2019/0345032 A1    Nov. 14, 2019

(30) Foreign Application Priority Data

Dec. 13, 2016   (NL) ...................... 2017988

(51) Int. Cl.
*C01B 7/07*    (2006.01)
*C01B 7/01*    (2006.01)
*C07H 1/00*    (2006.01)

(52) U.S. Cl.
CPC .............. *C01B 7/0712* (2013.01); *C01B 7/01* (2013.01); *C07H 1/00* (2013.01)

(58) Field of Classification Search
CPC ............ C01B 7/01; C01B 7/0712; C07H 1/00
See application file for complete search history.

(56) References Cited

U.S. PATENT DOCUMENTS 2,778,751 A   1/1957  Riehm
2,901,407 A   8/1959  Colton
(Continued)

FOREIGN PATENT DOCUMENTS

DE          362230 C    10/1922
EP        2368842 A1     9/2011
(Continued)

OTHER PUBLICATIONS

International Search Report dated Mar. 19, 2018 for PCT/EP2017/082219.

*Primary Examiner* — Ngoc-Yen Nguyen
(74) *Attorney, Agent, or Firm* — Suiter Swantz pc llo (57) ABSTRACT

A purified hydrochloric acid composition is prepared from a stream of a contaminated hydrochloric acid composition by a process comprising a distillation treatment, wherein at least a first distillation column is operated at a first pressure and a second distillation column is operated at a second pressure, which second pressure is lower than the first pressure; wherein the contaminated hydrochloric acid composition comprises water, contaminants and hydrochloric acid in a first hydrochloric acid concentration of above the azeotropic composition of hydrochloric acid and water at the first pressure; wherein a part of the stream of the contaminated hydrochloric acid composition is fed into the first distillation column to yield a first bottom product comprising water and hydrochloric acid with a hydrochloric acid concentration below the first hydrochloric acid concentration and a first top product comprising hydrochloric acid in a concentration above the azeotropic hydrochloric acid composition at the first pressure; wherein at least a portion
(Continued)

of the first bottom product is passed to the second distillation column; wherein another part of the stream of the contaminated hydrochloric acid composition is fed into the second distillation column to yield a second top product comprising contaminants and water, and a second bottom product comprising water and hydrochloric acid; wherein at least a part of the second bottom product is recycled into the first distillation column; and wherein the first top product is recovered as purified hydrochloric acid composition.

15 Claims, 1 Drawing Sheet

(56) References Cited

U.S. PATENT DOCUMENTS

| | | |
|---|---|---|
| 2,945,777 A | 7/1960 | Riehm |
| 3,394,056 A | 7/1968 | Nadler et al. |
| 3,548,282 A | 12/1970 | Schiller |
| 4,029,515 A | 6/1977 | Kiminki et al. |
| 4,199,371 A | 4/1980 | Regnault et al. |
| 4,762,537 A | 8/1988 | Fleming et al. |
| 5,174,865 A | 12/1992 | Stultz et al. |
| 5,316,998 A | 5/1994 | Lee et al. |
| 6,365,121 B1 * | 4/2002 | Wurmbauer ............ C23G 1/36 423/488 |
| 2011/0236296 A1 * | 9/2011 | Shimizu ................. B01D 3/14 423/488 |
| 2012/0227733 A1 | 9/2012 | Eyal et al. |
| 2012/0279497 A1 | 11/2012 | Jansen et al. |
| 2014/0308182 A1 * | 10/2014 | Weissenbaeck ......... C22B 3/10 423/139 |
| 2018/0208465 A1 * | 7/2018 | Tanimoto ................ B01D 3/36 |

FOREIGN PATENT DOCUMENTS

| | | |
|---|---|---|
| EP | 2371263 A1 | 10/2011 |
| EP | 2371763 A1 | 10/2011 |
| WO | 2016099272 A1 | 6/2016 |
| WO | 2016190739 A1 | 12/2016 |
| WO | 2017039439 A1 | 3/2017 |
| WO | 2017082723 A1 | 5/2017 |

* cited by examiner

PROCESS FOR PURIFYING A CONTAMINATED HYDROCHLORIC ACID COMPOSITION

FIELD

The present invention relates to a process for purifying a contaminated hydrochloric acid composition. In particular, the invention relates to a process for the purification of a contaminated hydrochloric acid composition by distillation treatment wherein at least two distillation columns at different pressures are used.

BACKGROUND

A contaminated hydrochloric acid (HCl) composition may be obtained in the hydrolysis of lignocellulosic material, wherein particulate lignocellulosic material is contacted with hydrochloric acid to yield a hydrolysate comprising saccharides, hydrochloric acid, water and contaminants. A known method includes the Bergius Rheinau process, as described in e.g. DE 362230 and U.S. Pat. No. 4,199,371. The operating temperature during the hydrolysis can be relatively low; the temperature can be around room temperature and is typically at most 110° C.

In the Bergius Rheinau process lignocellulosic material, such as wood, is shredded to chips or other particulate formats which are treated with a concentrated hydrochloric acid composition. During the treatment for instance about two-thirds of the wood is dissolved by the acid in the form of mono- and oligosaccharides, and the rest, e.g. about one-third remains as lignin. The dissolved fraction comprises mono- and oligosaccharides, together with water and hydrochloric acid. This fraction is generally referred to as the hydrolysate. From U.S. Pat. No. 4,029,515 it is known that the hydrolysate of lignocellulosic material also may comprise several by-products, including relatively volatile compounds that have boiling points below 120° C., such as acetic acid and methanol. According to U.S. Pat. No. 4,029,515 these by-products are especially derived from pentosans. These saccharides are present in the hemicellulose fraction of the lignocellulosic material. The lignin fraction is obtained as a solid fraction that comprises lignin, residual water and hydrochloric acid. After separation of the desired saccharides from the hydrolysate a contaminated HCl composition is obtained. It would be desirable to re-use this contaminated HCl composition. However, during the hydrolysis and during the treatments associated with the separation of the saccharides from the hydrolysate the HCl concentration of the contaminated HCl composition is lower than the HCl concentration of the concentrated HCl composition that was initially used for the hydrolysis. Such may especially be the case when the lignin fraction is washed to recover adsorbed hydrochloric acid and the washing liquid is combined with the remainder of the hydrolysate.

The hydrolysis of the lignocellulosic material may be conducted in two stages. In a first stage a so-called pre-hydrolysis is conducted, wherein the hemicellulose in the lignocellulosic material is digested, yielding a mixture, i.e. a pre-hydrolysate, comprising xylose, arabinose, mannose, glucose and their oligomers as saccharides. In a second stage, i.e., the main hydrolysis, the remaining carbohydrate portion of the lignocellulosic material that has been subjected to the pre-hydrolysis, consisting to a large extent of cellulose, is subsequently digested with more concentrated HCl, yielding mainly glucose and its oligomers as saccharides in the hydrolysate. Such a two-stage hydrolysis has been described in U.S. Pat. No. 2,945,777. This patent document describes that is was already known to conduct a pre-hydrolysis of wood using a dilute acid, e.g. a hydrochloric acid having a HCl concentration of 0.5 to 1.5% wt at elevated temperature, e.g. 120 to 140° C. The thus treated pre-hydrolyzed wood is then treated with concentrated hydrochloric acid. In the process according to U.S. Pat. No. 2,945,777 softwood sawdust is subjected to a pre-hydrolysis at about 15 to 30° C. with hydrochloric acid having an HCl concentration of 34 to 37% wt, and the pre-hydrolyzed sawdust is subsequently hydrolyzed in a main hydrolysis with hydrochloric acid having a HCl concentration above 40% wt.

In a conventional Bergius-Rheinau process HCl and water are separated from the hydrolysate via evaporation, as shown in Ind. Eng. Chem., 29 (1937) 247-253. In this way about 80% of the HCl is recovered. HCl vapors are condensed, washed and the acid is recycled. In this evaporation step also volatile organic contaminants such as methanol and acetic acid are also evaporated from the hydrolysate. An outlet needs to be provided for these volatile contaminants in order to prevent their build-up to unacceptably high levels in the recycled acid.

Further, a significant portion of the HCl that is used for the hydrolysis is adsorbed on the lignin. In order to recover this adsorbed HCl the lignin is typically washed with water, yielding a dilute HCl solution (cf. U.S. Pat. No. 2,778,751).

It is evident that it is desirable to recover both HCl from the HCl evaporation and from the dilute HCl solution and to enable the recycle of the HCl to the hydrolysis process. At the same time it is desirable to at least partly remove the volatile contaminants.

A possible method to purify a contaminated HCL composition would be via distillation. A one-stage distillation is generally unsatisfactory.

The purification of a hydrochloric acid (HCl) feed composition in a plurality of distillation stages is well-known. In U.S. Pat. No. 3,394,056 it has, for example, been described that substantially anhydrous HCl is separated from an aqueous HCl solution by subjecting the HCl solution first to a distillation that is operated at about atmospheric pressure and subjecting the bottom product of the first distillation to a second distillation that is operated at a higher pressure to obtain a highly concentrated HCl top product and bottom product that hardly contains any HCl. This process is based on the fact that the composition of the azeotrope of water and HCl moves towards higher water concentration as the pressure is elevated. Such a process is suitable for HCl compositions wherein the HCl concentration is below the azeotropic HCl concentration at the pressure of the first distillation.

In EP 2368842 a process for the purification of a contaminated HCl feed composition having an HCl concentration above the azeotropic HCl concentration under atmospheric pressure, is disclosed, wherein the HCl feed composition is subjected to distillation in a single distillation column, wherein the operating pressure is set such that the azeotropic HCl concentration under the operating pressure is higher than the HCl concentration in the contaminated HCl feed composition. The distillation of the contaminated HCl feed composition is therefore similar to the first distillation of the process according to U.S. Pat. No. 3,394,056.

A variation of such a purification process has been described in EP 2371763. According to this process a contaminated HCl feed composition that has an HCl concentration above the azeotropic HCl concentration at atmospheric pressure, is mixed with water or a dilute HCl solution to arrive at a composition with an HCl concentration below the azeotropic HCl concentration, and subjecting the thus obtained composition to distillation in a single distillation column operating at atmospheric pressure. It is evident that the processes of both EP 2368842 and EP 2371763 adapt the concentration of the contaminated HCl feed composition or the pressure of the distillation treatment such that the composition that is subjected to the distillation has an HCl concentration below the azeotropic HCl concentration at the pressure prevailing in the distillation operation.

The purification method described in EP 2371763 is not desirable for solving the problem of contaminated HCl compositions from processes as the Bergius Rheinau process, as dilution of the contaminated HCl composition from the hydrolysate and subsequent re-concentration may not be cost-effective. The purification method described in EP 2368842 is also not feasible. If the lower operating pressure in the distillation according to EP 2368842 would be contemplated, such would require the construction and operation of an expensive large low-pressure distillation column wherein the entire contaminated HCl composition is to be distilled. Moreover, the HCl concentration obtained in the exemplified distillation amounts to 21.9%, which is generally too low for a satisfactory hydrolysis.

A potential solution could be provided by the process described in U.S. Pat. No. 2,901,407. According to U.S. Pat. No. 2,901,407 a contaminated aqueous HCl solution is purified by passing this HCl solution into a first distillation zone, separating therefrom a vaporous fraction containing HCl and contaminants and a liquid fraction containing HCl and water wherein the HCl concentration is higher than in the original contaminated HCl solution, and passing the liquid fraction to a second distillation zone, operated at a higher pressure than the pressure in the first distillation zone, to yield a vaporous effluent comprising HCl and water and a liquid aqueous HCl solution of azeotropic concentration. A portion of the vaporous effluent from the second zone is introduced into the first distillation zone, and the remainder is partially condensed to yield anhydrous HCl vapor and an aqueous HCl fraction that is recycled to the second distillation zone. This process is known as the dual pressure distillation process. This dual pressure distillation process can work if the HCl concentration in the contaminated aqueous HCl solution is below the azeotropic HCl concentration. However, if the HCl composition of the contaminated aqueous HCl solution to the dual pressure distillation process is above the azeotropic HCl concentration, the above-described method is not feasible. This may occur if improvements to the hydrolysis process have been made that greatly reduce the flow of water into the process, resulting in a more concentrated contaminated HCl composition. Such improvements to the hydrolysis process have e.g. been described in WO 2016/099272, disclosing the recovery of saccharides by using a carrier oil, and in NL 2015374 (corresponding to WO2017/039439) describing the recovery of HCl from lignin by stripping with an aprotic gas. An option would seem to be the introduction of the contaminated aqueous HCl solution into the high pressure distillation zone, rather than the low pressure first distillation zone, so that an HCl rich product can be taken off the top. However, if this would be done, volatile organic contaminants such as methanol and acetic acid, will be taken off the top of the high pressure column together with the HCl, and recycled therewith. So a build-up of these volatile contaminants to unacceptably high levels might occur. The inventors set out to overcome these deficiencies.

DETAILED DESCRIPTION

Accordingly, the present invention provides a process for preparing a purified hydrochloric acid composition from a stream of a contaminated hydrochloric acid composition by a distillation treatment, wherein at least a first distillation column is operated at a first pressure and a second distillation column is operated at a second pressure, which second pressure is lower than the first pressure;

wherein the contaminated hydrochloric acid composition comprises water, contaminants and hydrochloric acid in a first hydrochloric acid concentration of above the azeotropic composition of hydrochloric acid at the first pressure;

wherein a part of the stream of the contaminated hydrochloric acid composition is fed into the first distillation column to yield a first bottom product comprising water and hydrochloric acid with a hydrochloric acid concentration below the first hydrochloric acid concentration and a first top product comprising hydrochloric acid in a concentration above the azeotropic hydrochloric acid composition at the first pressure;

wherein at least a portion of the first bottom product is passed to the second distillation column;

wherein another part of the stream of the contaminated hydrochloric acid composition is fed into the second distillation column to yield a second top product comprising contaminants and water, and a second bottom product comprising water and hydrochloric acid;

wherein at least a part of the second bottom product is recycled into the first distillation column; and wherein the first top product is recovered as purified hydrochloric acid (HCl) composition.

In accordance with this process a highly concentrated purified HCl composition is obtained as the top product of the first distillation column. The top product of the second distillation column, which may be relatively small, contains at least a portion of the contaminants that were present in the part of the contaminated HCl composition that was fed into this second distillation column. The additional treatment of the part of the contaminated HCl composition that is fed to the second distillation column establishes that contaminants and surplus water are adequately removed from the process. The pressure in the second distillation process is lower than the pressure in the first distillation column. Therefore, the azeotropic HCl concentration that is contingent to the lower pressure in the second distillation column will be higher than the azeotropic HCl concentration that belongs to the higher pressure in the first distillation column. Suitably, the second bottom product has an HCl concentration that is substantially equal to the azeotropic HCl concentration that is contingent to the pressure in the second distillation column. The second bottom product also suitably has a HCl concentration that is higher than the HCl concentration in the HCl composition or compositions that is or are fed into the second distillation column. It is desirable to arrange for the pressure difference between the two columns, and hence the difference in HCl-water azeotrope compositions, to be large enough to allow a minor portion of contaminated HCl feed to be sent to the lower pressure column, and still result in the average HCl feed composition to this column being sufficiently below the azeotropic composition to permit water and organic contaminants to be removed as top product.

The contaminated HCl composition comprises contaminants. As indicated above, at least some of the contaminants may be relatively volatile. In this specification it is understood that this means that these contaminants, as pure compounds, have atmospheric boiling points of below 120° C. In this way, the part of the second bottom product that is recycled to the first distillation column has a lower concentration of contaminants than the concentration of contaminants in the feed to the second distillation column. Preferably, the contaminants have been obtained in the hydrolysis of lignocellulosic material. Such contaminants may be the reaction products of the hydrolysis of the cellulose and/or hemicellulose chains which hydrolysis yields in particular glucose, mannose, galactose, arabinose and xylose as main products, in addition to which volatile contaminants may be formed. The main contaminants that are obtained in the hydrolysis of lignocellulosic material may comprise methanol and carboxylic acids with 1 to 4 carbon atoms, such as acetic acid. The contaminated hydrochloric acid composition preferably comprises water, hydrochloric acid and methanol and/or carboxylic acids having 1 to 4 carbon atoms, such as acetic acid, as contaminants. Some of these contaminants tend to have a boiling point below the boiling point of the azeotropic HCl composition of the second distillation column, and can therefore be easily separated via the top product. The contaminants that have a boiling point above the boiling point of the azeotropic HCl composition of the second distillation column may not be completely vaporized but these contaminants will at least partly be in the vapor phase. Therefore a portion of such contaminants will be removed from the second distillation column together with volatile contaminants. The amount of the contaminants may depend on the method in which the contaminated HCl composition is obtained. As indicated above, the hydrolysis of a lignocellulosic material is a preferred method to produce the contaminated HCl composition. The hydrolysis of lignocellulosic material may be carried out in a number of ways as is known in the art, e.g., by performing a pre-hydrolysis and a main hydrolysis. Alternatively, a single hydrolysis method may also be carried out. The contaminated HCl composition suitably comprises contaminants in an amount of 0.1 to 25% wt, preferably from 0.25 to 15% wt, or possibly even from 0.1 to 5% wt (percent by weight), based on the contaminated HCl composition.

The stream of contaminated HCl composition is partially fed into the first distillation column. The first distillation column is operated at a pressure higher than the pressure in the second distillation column. The azeotropic composition is dependent on the pressure. In order to be most effective, the first HCl concentration of the contaminated HCl composition and/or the pressure in the first distillation column are suitably selected such that the first HCl concentration in the contaminated HCl composition is higher than the azeotropic HCl composition prevailing at that pressure. Typically, the contaminated hydrochloric acid composition comprises a first hydrochloric acid concentration of in the range of 25 to 50% wt, based on the amount of water and hydrochloric acid. In order to achieve an azeotropic HCl composition that is below the first HCl concentration the first distillation column is suitably operated at a first pressure in the range of 1 to 20 bar, preferably 3 to 10 bar, more preferably from 4 to 8 bar. The temperature in the first distillation column (also referred to herein as the first temperature) may suitably be in the range of 100 to 350° C. Under such distillation conditions the first top product may comprise an enriched HCl composition, or even be substantially pure HCl, and the first bottom product may be a liquid having the azeotropic HCl composition at the pressure in the first column. If substantially pure gaseous HCl is the desired product such may be accomplished in the process of the present invention. The achievement of pure gaseous HCl may then require an intense distillation treatment with a significant number of theoretical trays. Such an intense treatment may add to costs and effort. In many instances the first top product does not need to constitute of pure gaseous HCl. It may be sufficient to obtain a concentrated mixture of HCl and water. The distillation may be less severe to obtain such a mixture. Suitably, the top product may comprise from 60 to 100% wt of HCl, more conveniently from 70 to 95% wt, based on a mixture of HCl and water, if present. The first top product may also comprise some volatile contaminants. However, the amount of contaminants will be reduced compared to the amount of contaminants in the stream of contaminated hydrochloric acid composition that is subjected to the distillation treatment. Since also a part of the stream of contaminated HCl composition is fed into the second distillation column, the contaminants that are fed into the second distillation column will be removed from the process via the top product of the second distillation column. That means that at least a significant portion of the contaminants are removed from the process, so that no detrimental build-up of contaminants occurs. The amount of contaminants may be reduced by withdrawing a small stream from the first distillation column at a position below the position where the top product is withdrawn. However, when the amount of contaminants is relatively small the contaminants may be left in the first top product without involving a significant detrimental effect in the remainder of the process.

The proportion of the stream of contaminated HCl composition that is passed into the first distillation column may vary between wide ranges. The skilled person will typically select the most effective division between the part that is sent to the first distillation column and the part that is fed into the second distillation column. One parameter that may influence this division is the amount of contaminants in the stream of contaminated HCl composition. When the amount is low, e.g. from 0.1 to 2% wt, the part that is fed into the second distillation column will suitably be smaller than when the amount of contaminants is above 2% wt. Suitably the part of the stream of the contaminated hydrochloric acid composition that is fed into the first distillation column constitutes from 10 to 90% wt of this stream. When the level of the contaminants in the contaminated HCl composition is at most 2% wt, a major part of the stream of contaminated HCl composition will suitably be passed to the first distillation column. Such a major part may suitably be from 10 to 90% wt, preferably from 50 to 90% wt, more preferably from 60 to 85% wt, of the stream of contaminated HCl composition. The proportion of the stream of contaminated HCl composition that is passed to the second distillation column may suitably vary from 90 to 10% wt, preferably from 50 to 10% wt, more preferably from 40 to 15% wt. When the contaminated HCl composition comprises at most 2% wt contaminants, the proportion of the stream that is passed to the second distillation column may suitably be in the range of 50 to 10% wt.

The part of the stream that is fed into the first distillation column is separated in a relatively HCl-rich first top product and a relatively HCl-depleted first bottom product. At least part of this first bottom product is suitably passed to the second distillation column. A part of the bottom product may be re-boiled and recycled to the first distillation column. The part that is not re-boiled is suitably fed in its entirety to the second distillation column. This part is subjected to the distillation conditions that are applied in the second distillation column, together with the part of the stream of contaminated HCl composition that is also fed into the second distillation column. These parts may be fed into the second distillation column at different positions of the column. However, it is more convenient to combine the parts into one stream and feed to combined stream into the second distillation column. The part of the stream of the contaminated hydrochloric acid composition that is fed into the second distillation column preferably constitutes from 10 to 90% wt of the stream of the contaminated hydrochloric acid composition. A skilled person may determine what proportion of the contaminated HCl composition is fed into the second distillation column dependent on a number of properties, such as the amount of contaminants, the nature and volatility of the contaminants, the amount of water to be removed from the process and the concentration of HCl in the top product of the first distillation column. When the part of the stream that is fed into the second distillation column is below 10% wt there is a risk that too many of the contaminants are passed into the first distillation column and the removal of the contaminants is not effective. When the proportion of the stream that is fed into the second distillation column is more than 90% wt of the stream of contaminated HCl composition there is a risk that the concentration of HCl in the feed to the second distillation column is so high that it is infeasible to obtain a sufficiently low pressure for corresponding to the desired azeotropic concentration. The second distillation column is to be operated such that as second top product a mixture of contaminants and water is obtained wherein the concentration of contaminants is higher than in the stream of contaminated HCl composition. The second bottom product is to comprise HCl and water in a composition wherein the amount of HCl is higher than in the first bottom product that is fed into the second distillation column. When the proportion of the stream of contaminated HCl composition that is fed into the second distillation column is more than 90% wt of the stream of contaminated HCl composition, the HCl concentration in the second distillation column may be so high that it is virtually impossible to obtain a relatively concentrated HCl-water mixture as second bottom product.

The operating conditions of the second distillation column may depend on the HCl concentration in the combined streams that are fed as feedstock into the second distillation column. The pressure is suitably selected such that the azeotropic product of HCl and water is obtainable as bottom product. Typically, the second distillation column is operated at a pressure in the range of 0.05 to 0.9 bar, preferably from 0.1 to 0.5 bar. It is feasible to operate at a lower pressure, but lowering of the pressure to values below 0.05 bar merely adds to the costs. The upper limit of 0.9 bar is selected to create a sufficient pressure difference between the first and the second distillation columns. At the pressure of 0.05 to 0.9 bar, the distillation temperature in the second distillation column (also referred to herein as second temperature) is suitably in the range of 40 to 99° C. The pressure difference between the first and the second distillation columns is suitably from 0.1 to 20 bar, preferably from 0.2 to 15 bar, more preferably from 0.5 to 10 bar, and most preferably from 1 to 8 bar.

The second distillation column is suitably operated such that the second top product is not only enriched in contaminants, but is also substantially free from HCl. In this way, not only losses of HCl are prevented, but also the work-up of the second top product, if any, comprising the contaminants and water is facilitated. That makes it desirable to operate the second distillation column such that all HCl that is fed into the second distillation column is separated therefrom via the second bottom product. The second bottom product may have an HCl concentration of up to the azeotropic HCl composition. Typically, the second bottom product has a hydrochloric acid concentration in the range of 15 to 40% wt of hydrochloric acid, based on the amounts of hydrochloric acid and water. Preferably, the second bottom product has an HCl concentration of the azeotropic composition corresponding with the pressure that prevails in the second distillation column.

The second distillation column may be operated with the partial stream of the contaminated HCl composition and with at least a part of the first bottom product only. However, it is also possible to add other streams into the same distillation column. That is especially suitable if another stream of HCl and water is present in the process which stream would benefit from purification and if such other stream does not increase the HCl concentration to a level above the azeotropic composition at the pressure in the second distillation column. Therefore, it is advantageous in such cases that a second stream of hydrochloric acid and water is fed into the second distillation column.

The second stream of HCl and water may have an HCl concentration that may suitably be below the azeotropic HCl composition at the pressure that prevails in the second distillation column. Such is, however, not required. It is preferable that the combination of all streams that are fed into the second distillation have an overall HCl concentration below the azeotropic HCl composition. Each stream individually may, however, have a higher HCl concentration. Therefore, the second stream of hydrochloric acid and water suitably has a hydrochloric acid concentration in the range of 15 to 35% wt of hydrochloric acid, based on the amounts of hydrochloric acid and water.

As indicated above, the addition of such a second stream is advantageous if purification of such a second stream is desirable. The second stream of HCl and water therefore may further comprise contaminants. It is also advantageous if these contaminants are at least similar to the contaminants that are present in the stream of contaminated HCl composition. The contaminants in the second stream of HCl and water, therefore, suitably comprise volatile contaminants as defined above, and preferably comprise methanol and/or carboxylic acids, suitably with 1 to 4 carbon atoms, such as acetic acid. Such a second stream of HCl and water may become available in the hydrolysis of lignocellulosic material. Accordingly, the contaminated hydrochloric acid composition suitably originates from the hydrolysis of a lignocellulosic material. Advantageously, the second stream of HCl and water is obtained from the pre-hydrolysis of lignocellulosic material, wherein in a relatively short run, saccharides such as xylose, arabinose, galactose, mannose and glucose are liberated from the lignocellulosic material, yielding a pre-hydrolysate containing HCl, water, xylose, arabinose, galactose, mannose, glucose and contaminants. Without wishing to be bound by any theory, it is believed that in the pre-hydrolysis hemicellulose that is present in lignocelluosic material, is hydrolyzed. Hydrolysis of hemicellulose yields sugars such as xylose, arabinose, galactose and mannose. As hemicellulose also comprises sugars in acidified form, other components such as glucuronic acid and acetic acid may be obtained. Thereafter the solid residue of the pre-hydrolysis is subjected to the main hydrolysis wherein glucose is freed up from cellulose in this solid material. The main hydrolysis yields a main hydrolysate comprising saccharides, amongst which glucose is the most abundant. The pre-hydrolysate may be separated into saccharides, i.e. xylose and glucose, and a remaining liquid. The remaining liquid can be used as the second stream of HCl and water in the process of the present invention. In the pre-hydrolysis the treatment with concentrated HCl achieves the dissolution of a relatively large proportion of contaminants in the pre-hydrolysate. The second stream of HCl and water that originates from the pre-hydrolysate may comprise contaminants in the range of 4 to 35% wt. Since this second stream is advantageously fed into the second distillation column the large amount of contaminants are directly subjected to the distillation in the second column so that a large proportion of the contaminants are discharged from the process via the second top product. At the same time, the mixture of HCl and water in the second stream is subjected to the concentration of HCl via the recycle of the second bottom product to the first column.

The stream of contaminated HCl composition is suitably obtained in a process for the hydrolysis of a lignocellulosic material wherein particulate lignocellulosic material is contacted with hydrochloric acid to yield a hydrolysate comprising saccharides, hydrochloric acid, water and contaminants, wherein saccharides are separated from the hydrolysate to leave the contaminated hydrochloric acid composition. Accordingly, the present invention also provides a process for the hydrolysis of a lignocellulosic material
wherein particulate lignocellulosic material is contacted with hydrochloric acid to yield a hydrolysate comprising saccharides, hydrochloric acid, water and contaminants,
wherein saccharides are separated from the hydrolysate to leave a contaminated hydrochloric acid composition,
wherein optionally, the hydrochloric acid concentration in the contaminated hydrochloric acid composition is increased,
wherein the contaminated hydrochloric acid composition, optionally after having been subjected to an increase in the hydrochloric acid concentration, and having a first hydrochloric acid concentration, is subjected to a distillation treatment, wherein at least a first distillation column is operated at a first pressure and a second distillation column is operated at a second pressure, which second pressure is lower than the first pressure;
wherein the first hydrochloric acid concentration is above the azeotropic composition of hydrochloric acid and water at the first pressure;
wherein a part of the stream of the contaminated hydrochloric acid composition is fed into the first distillation column to yield a first bottom product comprising water and hydrochloric acid with a hydrochloric acid concentration below the first hydrochloric acid concentration and a first top product comprising hydrochloric acid in a concentration above the azeotropic composition at the first pressure;
wherein at least a portion of the first bottom product is passed to the second distillation column;
wherein another part of the stream of the contaminated hydrochloric acid composition is fed into the second distillation column to yield a second top product comprising contaminants and water, and a second bottom product comprising water and hydrochloric acid;
wherein at least a part of the second bottom product is recycled into the first distillation column; and
wherein the first top product is at least partly recycled and at least partly contacted with the particulate lignocellulosic material.

As indicated above, the hydrolysis of particulate lignocellulosic material is advantageously carried out by performing a pre-hydrolysis followed by a main hydrolysis. Therefore the particulate lignocellulosic material is preferably the product of a pre-hydrolysis of, optionally dried, lignocellulosic material with hydrochloric acid which yields the particulate lignocellulosic material and a pre-hydrolysate, comprising saccharides, hydrochloric acid, water and contaminants. The pre-hydrolysate is then suitably subjected to a separation step wherein saccharides are separated from the pre-hydrolysate to yield a second stream of hydrochloric acid and water, which second stream is fed into the second distillation column.

The pre-hydrolysate may be subjected to saccharides recovery in a separate treatment from the saccharides recovery from the main hydrolysate. The hydrolysates may also be combined and the saccharides may be recovered in one single treatment. Although in this way a single recovery is required, the admixture of xylose, arabinose, galactose, mannose and glucose may complicate any subsequent separation. Since the main hydrolysate mainly comprises glucose it is advantageous to recover the saccharides from the main hydrolysate separately from the pre-hydrolysate.

The separation of the saccharides from either the pre-hydrolysate or the main hydrolysate or the combined hydrolysates may be carried out in a manner known in the art. A possible way is by multi-stage vacuum evaporation of HCl and water, with steam stripping of HCl in the final stage. A disadvantage is that a rather diluted HCl solution is obtained which requires significant and expensive re-concentration. The separation may also be conducted as described in DE 362230 by treatment with a liquid heat carrier. Suitably, the separation is carried out as described in co-pending application NL 2015746, corresponding to WO 2017/082723. Accordingly, in the process for the hydrolysis of a lignocellulosic material as described above, saccharides are suitably separated from the hydrolysate to leave a contaminated hydrochloric acid composition, by;
  in a mixing zone admixing the hydrolysate with a carrier liquid in which the saccharides are insoluble and that has a boiling point higher than that of water to obtain an aqueous admixture;
  removing an aqueous phase from the aqueous admixture to obtain a first carrier liquid phase comprising carrier liquid, by-products and saccharides;
  separating the saccharides from the first carrier liquid phase to obtain a crude carrier liquid, comprising by-products and carrier liquid, and a saccharide product,
  wherein the process further comprises:
  subjecting at least a portion of the crude carrier liquid to a liquid-liquid extraction with a first solvent to obtain a by-product-rich solvent phase and a by-product-lean carrier liquid phase; and
  recycling at least a portion of the by-product-lean carrier liquid phase to the mixing zone.

The aqueous phase that has been removed from the aqueous admixture is fed to the process of the present invention as the stream of contaminated HCl composition.

When the pre-hydrolysate is treated separately from the main hydrolysate, the pre-hydrolysate may be subjected to a similar treatment wherein the hydrolysate is replaced by the pre-hydrolysate and the aqueous phase that is removed from the aqueous admixture can be used as the second stream in the process according to the present invention.

Suitably, the saccharides predominantly comprise glucose. For certain applications fructose is the desired saccharide. In such a case a glucose-containing solution may be subjected to isomerization. The isomerization of glucose to fructose is known in the art. The isomerization typically takes place in an aqueous environment and is commonly catalyzed by alkaline compounds. The isomerization may also be conducted in the presence of one or more alcohols, e.g. in a methanol-containing solvent. The mixture of fructose and glucose that is then obtained may be isolated by means of evaporation or by means of the addition of an anti-solvent. The most common anti-solvent is ethanol. A suitable method has been described in Crestani et al., "Integration of the process of fructose crystallization by addition of anti-solvent", Proceedings of the 18$^{th}$ International Symposium on Industrial Crystallization ISIC 18; ETH Zurich, 2011, vol. 1, pp 1-6. Preferably, a mixture of glucose and fructose in a methanol- and/or water-containing composition is subjected to the addition of an anti-solvent to yield a mixture comprising solid fructose and glucose, which mixture of solid glucose and fructose thus obtained is subjected to selective dissolution of fructose in accordance with the process described in WO 2016/190739.

After the hydrolysis typically a lignin residue is obtained. Such lignin residue may still comprise some HCl. In order to recover also this hydrochloric acid the lignin residue may be treated in any known manner. One suitable manner is to wash the lignin with water to obtain a dilute hydrochloric acid solution. The HCl solution thus obtained may be re-concentrated, although that requires considerable effort and costs. The lignin may also be contacted with an organic solvent that is scarcely soluble in water to yield a mixture of solid lignin and an extractant solution comprising HCl, water and the solvent. Subsequently, the HCl, water and the solvent in the extractant solution are evaporated yielding a lignin composition with a reduced water and HCl content. Such a procedure has been described in US 2012/0279497 and US 2012/0227733. Preferably, the lignin residue is subjected to a drying treatment that is described in co-pending application NL 2015374, corresponding to WO2017/039439. In accordance with such a treatment HCl is recovered from the lignin residue that comprises lignin, water and hydrochloric acid by contacting the lignin residue with a stream of stripping gas stream comprising an aprotic gas to obtain an acidified vapor stream that comprises water vapor, hydrochloric acid and aprotic gas; and recovering HCl from the acidified vapor stream. Before contacting the lignin residue with the stripping gas it may suitably be heated, preferably to a temperature in the range of 150 to 280° C. There are several methods for achieving the recovery of HCl. One suitable method involves passing the acidified vapor stream along an adsorbent that selectively adsorbs hydrochloric acid, which can be followed by desorption. Typically such adsorbents include metal oxides that have a significant surface area, e.g. a BET surface area of at least 200 m$^2$/g. Suitable adsorbents include alumina, zeolite-alumina mixtures and alumina that is promoted with an alkali metal oxide. Examples of such adsorbents are disclosed in, e.g., U.S. Pat. Nos. 4,762,537 and 5,316,998. Adsorbents are most commonly used as means to purify contaminated gas streams. Their capacity therefore tends to be rather limited. If large amounts of hydrochloric acid are to be recovered from a large acidified vapor stream the equipment for the adsorbents must be large, too. The sheer size of such equipment may render the recovery very expensive. Therefore, it is preferred to subject the acidified vapor stream to absorption with a liquid wherein the hydrochloric acid is selectively dissolved. The liquid may consist of organic compounds, such as amines. Suitable amines include alkanolamines, di- and tri-alkyl amines. The amines may be primary, secondary and tertiary amines and may have at least 6, preferably at least 10, and more preferably at least 14, carbon atoms and at least one hydrophobic group. Examples of such amines are di-isopropanol amine, methyl diethanol amine, triethanol amine, tri(2-ethylhexyl)amine, tri-octyl amine, tri-isooctyl amine, tridecylamine, tricaprylyl amine and combinations thereof. Other suitable amines are listed in U.S. Pat. No. 3,548,282. It has been found that the hydrochloric acid may also be easily absorbed in an aqueous absorbent. Therefore, the acidified vapor stream is preferably subjected to absorption with an aqueous absorbent, to yield acid-loaded absorbent. The aqueous absorbent comprises water. The aqueous absorbent that is loaded with HCl may then be sent to the second distillation column for recovery of HCl.

The purified hydrochloric acid composition preferably comprises
from 85 to 95% wt of hydrochloric acid;
from 5 to 15% wt of water;
from 0.001 to 0.1% wt of methanol; and
from 0.25 to 4% wt of acetic acid,
the percentages being based on the amounts of methanol, acetic acid, water and hydrochloric acid.

This composition makes the purified hydrochloric composition excellently suitable for use in the digestion of lignocellulosic material. The HCl concentration is so high that the desired concentration of HCl can be easily obtained by dilution with water or any other aqueous stream that is available in the process. The level of the amounts of acetic acid and methanol is low enough to allow for any further dilution with water or any other aqueous process stream so that the resulting amounts of these contaminants in the eventual hydrochloric acid compositions are not so high that they may cause a build-up of contaminants in the re-concentration of the contaminated HCl compositions.

Figure 1:
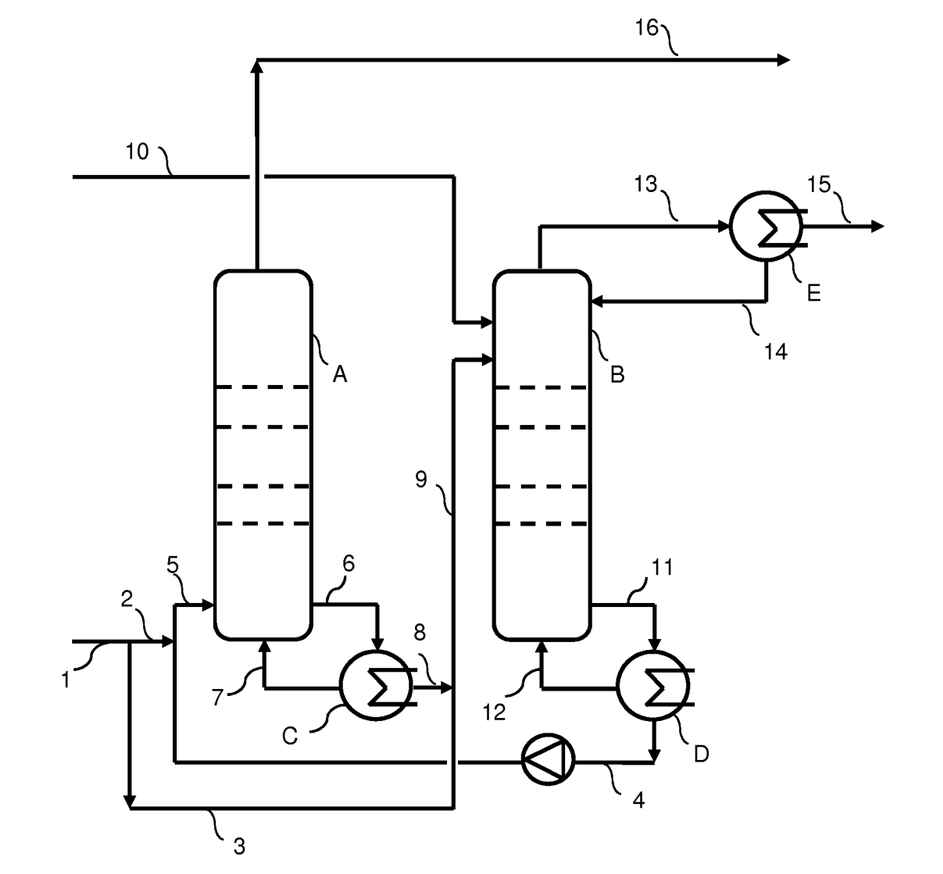
The sole FIGURE is the flow diagram of the process.

The invention will be illustrated by reference to the FIGURE.

The FIGURE shows a stream of contaminated hydrochloric acid composition that is fed via line [1] towards a first distillation column A. The stream of contaminated hydrochloric acid (HCl) composition has suitably been obtained in a Bergius-Rheinau process for the hydrolysis of a lignocellulosic material wherein particulate lignocellulosic material has been contacted with hydrochloric acid to yield a hydrolysate comprising saccharides, hydrochloric acid, water and contaminants. From such hydrolysate the saccharides are separated to leave the contaminated hydrochloric acid composition.

About four fifth (80% wt) of the stream in the line [1] is passed via a line [2] towards the distillation column A whilst about one fifth (20% wt) of the stream in the line [1] is separated therefrom and passed further via a line [3]. The stream in the line [2] is combined with a recycle stream in a line [4] and the combined streams are fed into the distillation column A via a line [5]. The pressure in the column A is selected such that the azeotropic composition at this pressure has a lower HCl concentration than the HCl concentration in the line [5]. For example, the HCl concentration in the line [5] may be about 23%. The pressure in the distillation column A will then be e.g. about 6 bar, so that a first top product is obtained with a HCl concentration above the HCl concentration in the azeotropic composition at 6 bar, whereas the first bottom product may have a HCl concentration of about the azeotropic HCl concentration. The pressure also has an influence on the temperature in the distillation column A. At 6 bar and an HCl concentration of about 23%, the temperature in the distillation column may vary from about 165° C. at the bottom and about 130° C. at the top of the column.

From the bottom of the first distillation column A a first bottom product is withdrawn via a line [6]. A part thereof of is heated in a re-boiler C and passed back into the distillation column A via a line [7]. The remainder of stream [6] is withdrawn via a line [8] and combined with the stream in the line [3] and fed into the upper part of a second distillation column B via a line [9]. The second distillation column is operated at a pressure that corresponds with an azeotropic composition wherein the HCl concentration is higher than the concentration of the feedstock. The feedstock may consist of the stream in the line [9] only. However, when the Bergius-Rheinau process is operated with a pre-hydrolysis and a main hydrolysis, it is also practical to also feed the HCl stream from the pre-hydrolysis into the second distillation column B, if the latter HCl stream has a concentration that would still have a combined HCl concentration below the azeotropic composition. In the FIGURE it is shown that a stream [10], coming from a pre-hydrolysis step in the Bergius-Rheinau process, is also fed into the upper part of the second distillation column B. Whereas in the FIGURE two separate streams are fed into the distillation column B, it is evident that the streams may be combined before introduction into the column. The size of the streams, the HCl concentrations therein and the pressure in the second column B can be accommodated such that the resulting HCl concentration of the combination of the streams [9] and [10] is below the azeotropic composition at the prevailing pressure in the column B. Hence, it is feasible that a stream from the pre-hydrolysis of lignocellulosic material has an HCl concentration of about 29% wt, and the stream in the line [9] has an HCl concentration of about 17% wt. The sizes of the streams are such that the overall HCl concentration of the combined feedstock amounts to about 18% wt. The column B is operated at a pressure in the range of 150 to 250 mbar, such that the azeotropic composition comprises about 20% wt. The second bottom product is withdrawn from the second column B via a line [11]. A part thereof is re-boiled in a re-boiler D and recycled to the column B via a line [12]. The other part is via the lines [4] and [5] recycled to the first column A. The HCl concentration in the line [4] is about the azeotropic concentration and amounts to about 18% wt. The second top product comprises water and some of the contaminants, such as acetic acid and methanol. This second top product is withdrawn from the column B via a line [13]. After condensation in a cooler E part of the second top product is recycled to the column B via a line [14] whereas the remainder, which is substantially free from HCl, is subjected to further waste water treatment via a line [15]. The water may be freed from the contaminants. By the removal of these contaminants the build-up of such contaminants is avoided.

The first top product from the first column A is withdrawn from the column via a line [16]. This product is enriched in HCl. The percentage of HCl in this top product may be as high as 90% wt. The stream from the line [16] may be admixed with make-up HCl and/or be mixed with water to obtain aqueous HCl compositions that are suitable for the pre-hydrolysis and/or main hydrolysis of lignocellulosic material in the Bergius-Rheinau process.

EXAMPLE

In an embodiment as shown in the FIGURE a stream of contaminated HCl composition amounting to 7,677 kg/h is passed through the line [1]. The stream comprises 3,110 kg/h HCl and 4,422 kg/h water, the balance being methanol (23 kg/h) and acetic acid (122 kg/h). The stream is split into a part comprising 81.4% wt (6,248 kg/h) that is forwarded via the line [2] and a part of 18.6% wt (1,429 kg/h) that is forwarded via the line [3]. The stream in the line [2] is combined with a recycle stream that is supplied via the line [4]. The stream in the line [4] amounts to 42,263 kg/h, with 31.751 kg/h water, 8,440 kg/h HCl, 2,066 kg/h acetic acid and 6 kg/h methanol. The combined stream is passed via the line [5] to the first distillation column A which operates at 6 bar. The temperature ranges from about 128° C. at the top and 164° C. at the bottom. The top product of the first distillation column A amounts to 3,994 kg/h, consisting of 398 kg/h water, 3,557 kg/h HCl, 38 kg/h acetic acid and 2 kg/h methanol. This top product is recovered as purified HC: composition via the line [16]. Via the line [8] the part of the bottom product that is not re-boiled and recycled to the distillation column A, amounting to 5,217 kg/h, is combined with the composition in the line [3]. The composition of the bottom product is 4,761 kg/h water, 376 kg/h acetic acid and 79 kg/h methanol. The combined streams are fed into the second distillation column B. Via the line [10] a HCl composition that results from a pre-hydrolysis of wood and consisting of 737 kg/h water, 447 kg/h HCl, 292 kg/h acetic acid and 58 kg/h methanol is also fed into the second distillation column B. The operating pressure in the column B is 200 mbar and the temperature ranges from 70° C. at the bottom to 59° C. at the top. From the top an aqueous contaminant stream is withdrawn via the line [15], amounting to 4,761 kg/h water, 376 kg/h acetic acid and 79 kgh methanol. From the bottom a recycle stream is withdrawn via the line [4], amounting to 42,263 kg/h and having the composition as described above.

The results show that about 91% of the acetic acid and about 97.5% of the methanol that is fed into the process is removed via the second top product. Moreover, the results show that the first top product has a very high concentration of HCl, and that all HCl that is removed from the distillation process is withdrawn via the first top product.

The invention claimed is:

1. A process for preparing a purified hydrochloric acid composition from a stream of a contaminated hydrochloric acid composition by a distillation treatment, the process comprises:
   obtaining the contaminated hydrochloric acid composition, which comprises water, contaminants and hydrochloric acid in a first hydrochloric acid concentration;
   feeding a part of the stream of the contaminated hydrochloric acid composition into the first distillation column to yield a first bottom product comprising water and hydrochloric acid with a hydrochloric acid concentration below the first hydrochloric acid concentration and a first top product comprising hydrochloric acid in a concentration based on weight above the azeotropic hydrochloric acid composition at the first pressure;
   wherein the first distillation column is operated at a first pressure so that the first hydrochloric acid concentration of the contaminated hydrochloric acid composition is above the azeotropic composition of hydrochloric acid and water at the first pressure;
   feeding at least a portion of the first bottom product and another part of the stream of the contaminated hydrochloric acid composition to a second distillation column to yield a second top product comprising contaminants and water, and a second bottom product comprising water and hydrochloric acid;

wherein the second distillation column is operated at a second pressure that is lower than the first pressure and the hydrochloric acid concentration of the combined stream comprising the first bottom product and the contaminated hydrochloric acid composition in the second distillation is less than the azeotropic composition of hydrochloric acid and water at the second pressure;

wherein at least a part of the second bottom product is recycled into the first distillation column, wherein the concentration of the combination of the part of the stream of the contaminated hydrochloric acid composition fed into the first distillation column and the part of the second bottom product recycled into the first distillation column is above the azeotropic composition of hydrochloric acid and water at the first pressure; and wherein the first top product is recovered as the purified hydrochloric acid composition.

2. The process according to claim 1, wherein the contaminated hydrochloric acid composition comprises:
water, hydrochloric acid and methanol and/or carboxylic acids with 1 to 4 carbon atoms as contaminants.

3. The process according to claim 1, wherein the contaminated hydrochloric acid composition comprises:
contaminants in an amount of 0.1 to 25% wt, based on the contaminated hydrochloric acid composition.

4. The process according to claim 1, wherein the contaminated hydrochloric acid composition comprises:
a first hydrochloric acid concentration of in the range of 25 to 50% wt, based on the amount of water and hydrochloric acid.

5. The process according to claim 1, wherein the first distillation column is operated at a first pressure in the range of 1 to 20 bar and at a temperature in the range of 100 to 350° C.

6. The process according to claim 1, wherein the part of the stream of the contaminated hydrochloric acid composition that is fed into the first distillation column constitutes from 10 to 90% wt of this stream.

7. The process according to claim 1, wherein the another part of the stream of the contaminated hydrochloric acid composition that is fed into the second distillation column constitutes from 90 to 10% wt of this stream.

8. The process according to claim 1, wherein the second distillation column is operated at the second pressure in the range of 0.05 to 0.9 bar and at a temperature in the range of 40 to 99° C.

9. The process according to claim 1, wherein the second bottom product has a hydrochloric acid concentration in the range of 15 to 40% wt of hydrochloric acid, based on the amounts of hydrochloric acid and water.

10. The process according to claim 1, wherein a second stream of hydrochloric acid and water is fed into the second distillation column, wherein the concentration of the combined feed comprising the combined stream and the second stream of hydrochloric acid and water in the second distillation column is less than the azeotropic composition of hydrochloric acid and water at the second pressure.

11. The process according to claim 10, wherein the second stream of hydrochloric acid and water has a hydrochloric acid concentration in the range of 15 to 35% wt of hydrochloric acid, based on the amounts of hydrochloric acid and water.

12. The process according to claim 10, wherein the second stream of hydrochloric acid and water further comprises:
contaminants.

13. The process according to claim 12, wherein the contaminants in the second stream of hydrochloric acid and water comprise:
methanol and/or carboxylic acids with 1 to 4 carbon atoms.

14. A process for the hydrolysis of a lignocellulosic material comprising:
contacting a particulate lignocellulosic material with hydrochloric acid to yield a hydrolysate comprising saccharides, hydrochloric acid, water and contaminants, separating the saccharides from the hydrolysate to leave a contaminated hydrochloric acid composition having a first hydrochloric acid concentration, optionally, the first hydrochloric acid concentration is obtained after a hydrochloric acid concentration in the contaminated hydrochloric acid composition, feeding a part of the stream of the contaminated hydrochloric acid composition into the first distillation column to yield a first bottom product comprising water and hydrochloric acid with the hydrochloric acid concentration below the first hydrochloric acid concentration and a first top product comprising hydrochloric acid in a concentration based on weight above the azeotropic hydrochloric acid composition at the first pressure;

wherein the first distillation column is operated at a first pressure so that the first hydrochloric acid concentration of the contaminated hydrochloric acid composition is above an azeotropic composition of hydrochloric acid and water at the first pressure;

feeding at least a portion of the first bottom product and another part of the stream of the contaminated hydrochloric acid composition to the second distillation column to yield a second top product comprising contaminants and water, and a second bottom product comprising water and hydrochloric acid;

wherein the second distillation column is operated at a second pressure that is lower than the first pressure and the hydrochloric acid concentration of the combined stream comprising the first bottom product and the contaminated hydrochloric acid composition in the second distillation is less than the azeotropic composition of hydrochloric acid and water at the second pressure;

recycling at least a part of the second bottom product into the first distillation column, wherein a concentration of the combination of the part of the stream of the contaminated hydrochloric acid composition fed into the first distillation and the part of the second bottom product recycled into the first distillation column is above the azeotropic composition of hydrochloric acid and water at the first pressure; and recycling at least part of the first top product to the contacting step.

15. A purified hydrochloric acid composition comprising:
from 85 to 95% wt of hydrochloric acid;
from 5 to 15% wt of water;
from 0.001 to 0.1% wt of methanol; and
from 0.25 to 4% wt of acetic acid,
the percentages being based on the amounts of methanol, acetic acid, water and hydrochloric acid.

* * * * *